(12) United States Patent
Doan et al.

(10) Patent No.: US 6,907,296 B1
(45) Date of Patent: Jun. 14, 2005

(54) IMPLANTABLE CARDIAC LEAD HAVING CONVENIENT IMPLANT LOCATION IDENTIFICATION AND METHOD OF MANUFACTURE

(75) Inventors: Phong D. Doan, Stevenson Ranch, CA (US); John R. Helland, Saugus, CA (US); David E. Kistler, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 556 days.

(21) Appl. No.: 10/061,568

(22) Filed: Feb. 1, 2002

Related U.S. Application Data

(63) Continuation of application No. 09/504,608, filed on Feb. 15, 2000, now abandoned.

(51) Int. Cl.[7] ................................................. A61N 1/05
(52) U.S. Cl. ....................................................... 607/119
(58) Field of Search .............................. 607/119–132; 600/373–377

(56) References Cited

U.S. PATENT DOCUMENTS

| | | | |
|---|---|---|---|
| 4,202,351 A | 5/1980 | Biche | 128/696 |
| 4,357,947 A | * 11/1982 | Littleford | 607/125 |
| 4,401,127 A | * 8/1983 | Littleford | 607/125 |
| 4,947,568 A | 8/1990 | De Barbieri | 40/316 |
| 5,170,578 A | 12/1992 | Pampel | 40/316 |
| 5,187,887 A | 2/1993 | Mori et al. | 40/316 |
| 5,315,774 A | 5/1994 | Chompff | 40/316 |
| 5,489,275 A | * 2/1996 | Thompson et al. | 604/264 |
| 5,511,331 A | 4/1996 | Morosini | 40/316 |
| 5,824,030 A | * 10/1998 | Yang et al. | 607/122 |

* cited by examiner

*Primary Examiner*—George R. Evanisko

(57) ABSTRACT

An implantable cardiac lead suitable for placement in any one of a plurality of implant locations of the heart includes an identifier which identifies the implant location of the lead. The lead includes a lead body which carries a plurality of implant location indicators. The implant location indicators may be removable whereby the removal of all but one location indicator provides a unique indication of the lead implant location. The implant location indicators may alternatively be individually selectable to provide a unique indication of the implant location. Still further, the implant location indicators may comprise an implant location identifying system wherein each indicator provides a direct indication of a respective different one of the plurality of implant locations and is configured for individual placement, and for retainment, on the lead.

6 Claims, 5 Drawing Sheets

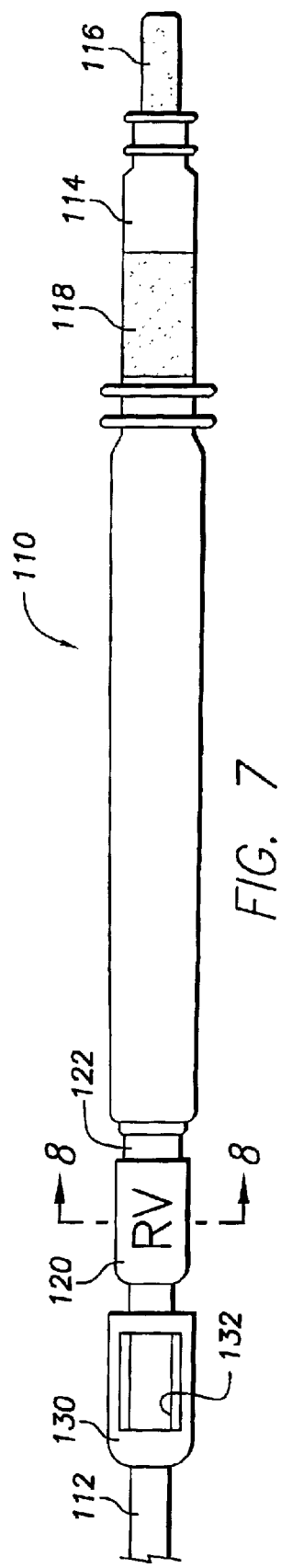
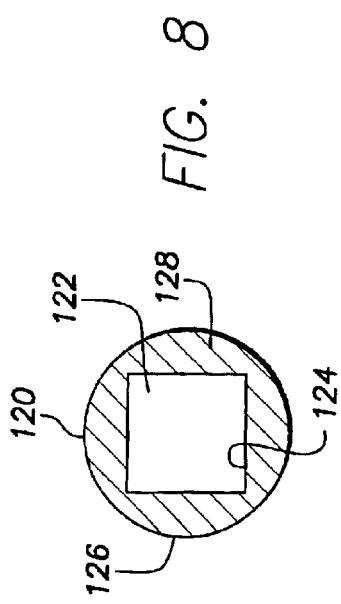
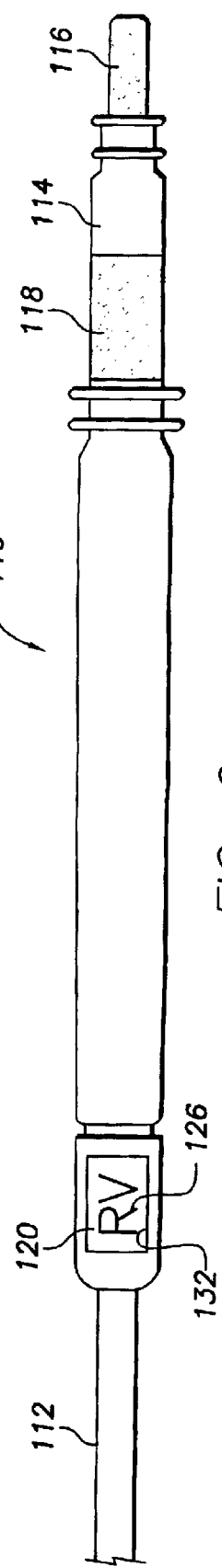
FIG. 7
FIG. 8
FIG. 9

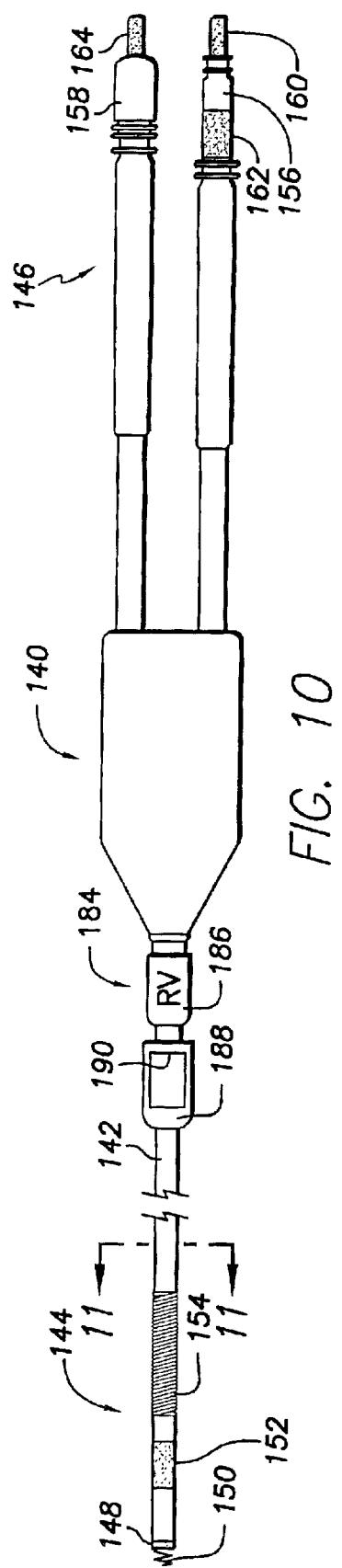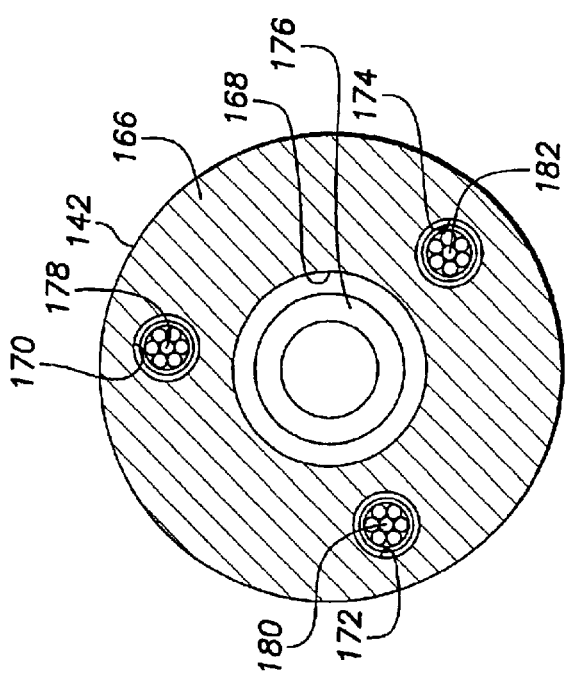

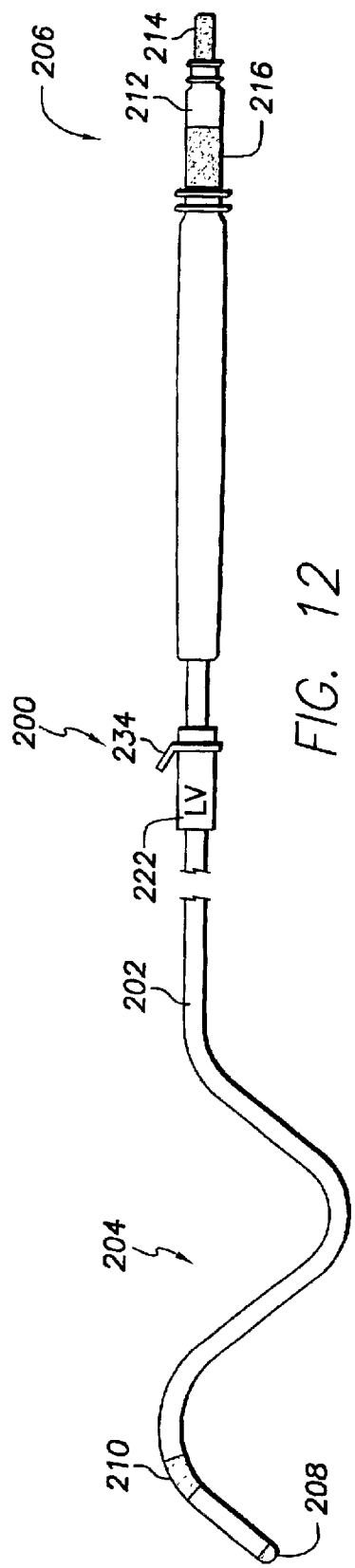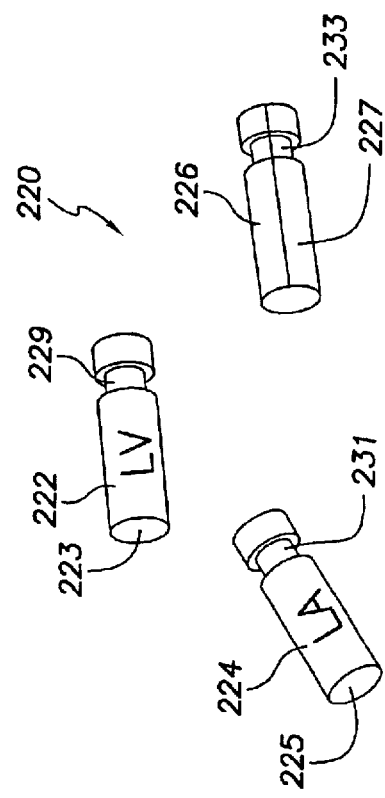
FIG. 12
FIG. 13

IMPLANTABLE CARDIAC LEAD HAVING CONVENIENT IMPLANT LOCATION IDENTIFICATION AND METHOD OF MANUFACTURE

CROSS-REFERENCE TO RELATED APPLICATIONS

This application is a continuation of U.S. patent application Ser. No. 09/504,608, filed Feb. 15, 2000, now abandoned.

FIELD OF THE INVENTION

The present invention is generally directed to an implantable cardiac lead. The present invention is more particularly directed to such a lead which is suitable for placement in any one of a plurality of implant locations of a heart and which includes an identifier at the lead proximal end to identify the implant location of the lead.

BACKGROUND OF THE INVENTION

Implantable cardiac leads are well known in the art. They find use, for example, in electrically coupling implantable cardiac monitors and implantable cardiac stimulation devices, such as implantable cardiac defibrillators (ICD's) or implantable pacemakers, to selected chambers of the heart. The leads may include one electrode, an electrode pair, or multiple electrodes, for sensing electrical activity of the heart and/or delivering pacing stimulation pulses to the heart. A lead may alternatively or additionally include one or more electrodes for delivering defibrillation pulses to a heart.

Most often, a patient receiving an implantable cardiac device will receive at least two implantable leads, one lead for positioning an electrode or electrodes in an atrium, and the other lead for positioning an electrode or electrodes in a ventricle of the heart. During the initial implant procedure of the implantable device or during device replacement, it is important for the physician to be able to keep track of the electrode implant locations of the leads.

Prior to the present invention, it has been difficult and time consuming for the physician to keep track of the electrode implant locations of the leads. In many instances, physicians had to rely on serial numbers or lead length values included in the serial numbers, placed upon the leads, to discern whether a lead is implanted in an atrium or a ventricle, for example. Implantable leads are of relatively small diameter, and as a result, the serial numbers placed on the leads have correspondingly small font size making them difficult to read and interpret. Still further, the presence of body fluid, such as blood, makes it even more difficult to read and interpret lead serial numbers. The situation is still further aggravated by the fact that many leads are used in or are designed for use in more than one implant location or chamber of the heart. This makes the serial numbers of such leads unreliable for electrode placement discernment.

SUMMARY OF THE INVENTION

The invention provides an implantable cardiac lead and a method of making an implantable cardiac lead having an identifier at the proximal end of the lead to readily identify the implant location of the lead in the heart.

In accordance with one embodiment, the lead is configured for location in any one of a plurality of implant locations of the heart. The lead is provided with a plurality of implant location identifiers, wherein each implant location identifier provides a direct indication of a respective different one of the plurality of implant locations.

In accordance with a further embodiment, the implant location indicators are individually removable whereby the removal of all but one location indicator enables a unique identification of the implant location of the lead.

Alternatively, each one of the plurality of implant location indicators is individually selectable to provide the unique identification of the electrode location.

The plurality of electrode implant location indicators may alternatively be provided as a system with the lead. Each indicator may be configured for retainment on the lead to provide a unique identification of the lead implant location in the heart.

BRIEF DESCRIPTION OF THE DRAWINGS

Further features and advantages of the present invention may be more readily understood by reference to the following description taken in conjunction with the accompanying drawings, in which:

FIG. 7 is a side plan view, to an enlarged scale, of the proximal end of an implantable cardiac lead including another embodiment of the present invention;

FIG. 8 is a sectional view taken along lines 8—8 of FIG. 7;

FIG. 9 is a side plan view, to an enlarged scale, of the lead of FIG. 7 after implant in accordance with the present invention;

FIG. 10 is a side plan view of still another implantable cardiac lead embodying the present invention;

FIG. 11 is a sectional view taken along lines 11—11 of FIG. 10;

FIG. 12 is a side plan view of an implantable cardiac lead including a still further embodiment of the present invention; and FIG. 13 is a perspective view of an implant location identifying system embodying further aspects of the present invention.

DETAILED DESCRIPTION OF THE PREFERRED EMBODIMENTS

Figure 1:
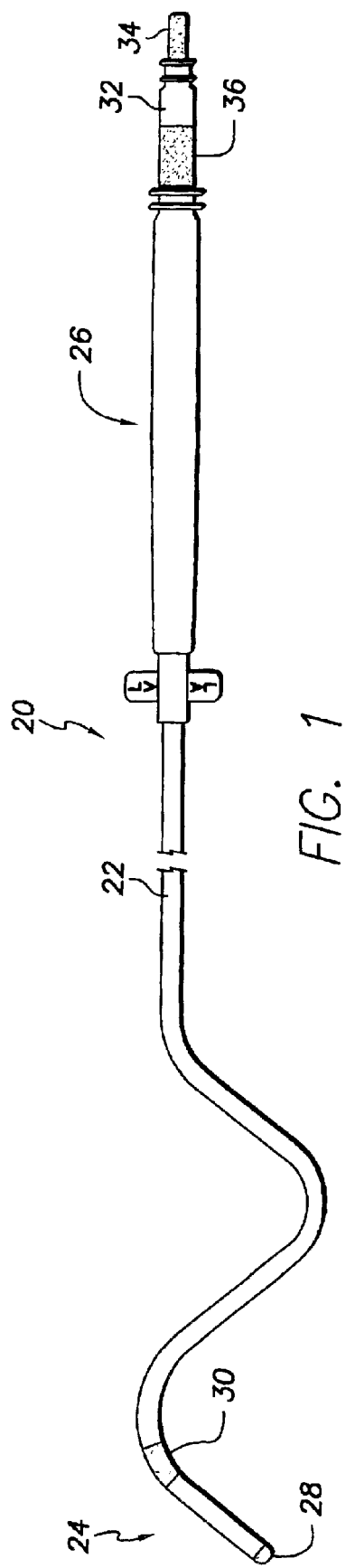
FIG. 1 is an exploded side plan view of an implantable cardiac lead embodying the present invention.

Referring now to FIG. 1, it illustrates an implantable cardiac lead 20 embodying the present invention. In accordance with this embodiment, the lead 20 is suitable for placement in the coronary sinus of the heart at one of a plurality of different lead implant locations of, for example, adjacent the left atrium or adjacent the left ventricle of the heart. The lead 20 generally includes an elongated lead body 22 having a distal end 24 and a proximal end 26. At the distal end 24, the lead body 22 has a pacing/sensing bipolar electrode pair including a tip electrode 28 and a ring electrode 30. At the proximal end 26, the lead body 22 has a connector 32. The connector 32 includes a connector pin terminal 34 and a connector ring terminal 36 which are coupled by lead conductors (not shown) to the tip electrode 28 and ring electrode 30 respectively in a manner well known in the art. The connector 32 is configured to be received within a complementarily shaped socket of an implantable cardiac device (not shown) in a manner known in the art for coupling the tip electrode 28 and ring electrode 30 to internal circuitry of the device.

Figure 2:
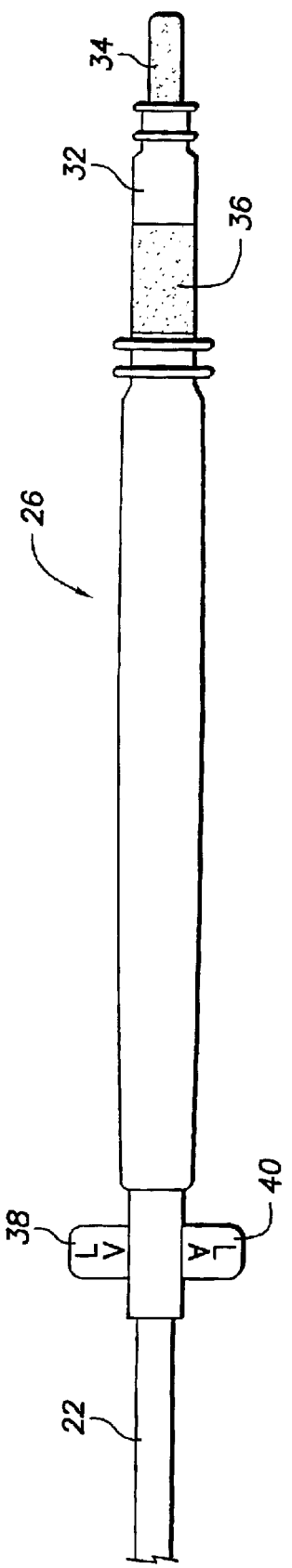
FIG. 2 is a side plan view, to an enlarged scale, of the proximal end of the lead of FIG. 1 illustrating the condition of the lead prior to implant in accordance with the present invention.

In accordance with the present invention, as may be seen more clearly with reference to FIG. 2, the proximal end 26 of the lead body 22 further includes a plurality of implant location indicators 38 and 40. Each of the implant location indicators includes a direct indication of a respective different one of the plurality of implant locations in which the electrodes 28 and 30, and hence the lead 20, may be implanted. For example, in accordance with this preferred embodiment, the indicator 38 includes a "LV" to provide a direct indication of the implant location within the distal coronary veins, overlying the left ventricle, and the indicator 40 includes a "LA" to provide a direct indication of the implant location within the coronary sinus vein adjacent the left atrium.

Each of the implant location indicators 38 and 40 is removable from the lead body 22. Hence, after the lead 20 is positioned in the desired lead implant location, the indicators not providing a direct indication of that location may be removed from the lead body 22 so that the remaining implant location indicator may provide a unique identification of the implant location of the lead 20 for future and ready reference. As an alternative, prior to positioning the lead 20 in the desired implant location, the indicators, which do not provide direction indication of the desired implant location, may be removed from the lead body 22. Similarly, with regards to subsequent embodiments described in the specification, an identifier may be manipulated on a lead in a manner based on an intended site prior to advancing the lead to the intended site.

Figure 3:
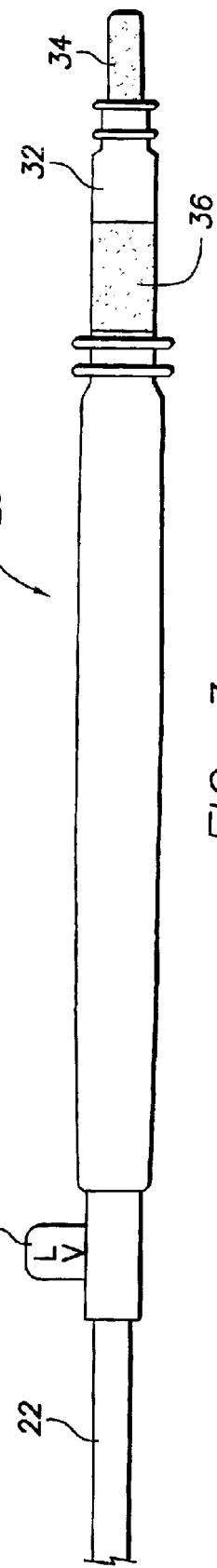
FIG. 3 is another side plan view, to an enlarged scale, of the proximal end of the lead of FIG. 1 illustrating the condition of the lead after implant in accordance with the present invention.

In accordance with this aspect of the present invention, FIG. 3 illustrate the lead 20 after it has been positioned in the distal coronary veins with the electrodes 28 and 30 overlying the left ventricle. To that end, the implant location indicator 40 no longer remains on the lead body 22 while the implant location indicator 38 is left to remain on the lead body 22 to indicate the left ventricular lead implant location.

The indicators 38 and 40 may be formed of relatively thin flexible suitable biocompatible material, such as silicone rubber. This permits each of the indicators to be readily removable by simply tearing the same from the lead body 22. Other, more rigid biocompatible materials as known in the art may also be used to form the indicators 38 and 40 and to provide ready removability.

Figure 4:
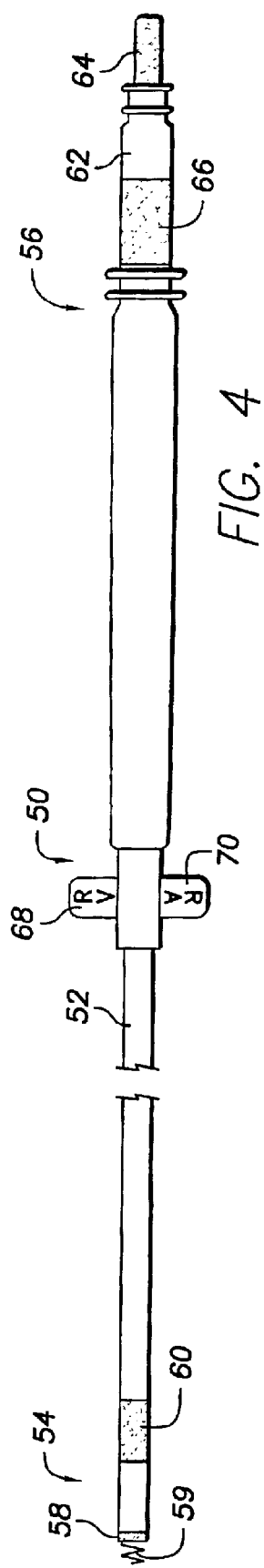
FIG. 4 is a side plan view of another implantable cardiac lead embodying the present invention.

Referring now to FIG. 4, it illustrates another implantable cardiac lead 50 embodying the present invention. In accordance with this embodiment, the lead 50 is suitable for placement in a plurality of different lead implant locations of the heart including the right atrium and the right ventricle. The lead 50 includes an elongated lead body 52 having a distal end 54 and a proximal end 56. At the distal end 54, the lead body 52 has a pacing/sensing bipolar electrode pair including a tip electrode 58 having a screw-in anchoring helix 59 of the type well known in the art, and a ring electrode 60. At the proximal end 56, the lead body 52 has a connector 62 including a connection pin terminal 64 and a connection ring terminal 66. The connection pin 64 and ring 66 are coupled by lead conductors (not shown) to the tip electrode 58 and ring electrode 60, respectively, in a manner well known in the art. The connector 62 is configured to be received within a complimentarily shaped socket of an implantable cardiac stimulation device (not shown) in a manner known in the art for coupling the tip electrode 58 and ring electrode 60 to internal sensing and pacing circuitry of the implantable device.

As in the embodiment of FIGS. 1–3, the proximal end 56 of the lead body further includes a plurality of implant location indicators 68 and 70. Each of the implant location indicators includes a direct indication of a respective different one of the plurality of implant locations in which the electrodes 58 and 60, and hence the lead 50, may be implanted. To that end, the indicator 58 includes a "RV" to provide a direct indication of the implant location within the right ventricle of the heart, and, the indicator 70 includes a "RA" to provide a direct indication of the implant location within the right atrium.

Each of the implant location indicators 68 and 70 is removable from the lead body 52. Hence, after the lead 50 is positioned in the desired lead implant location, the indicators not providing a direct indication of that location may be removed from the lead body 52 so that the remaining implant location indicator may provide a unique identification of the implant location of the lead. For example, if the lead 50 has been positioned in the right ventricle, the implant location indicator 70 may be removed from the lead body 52 to leave the implant location indicator 68 on the lead body 52 for indicating the right ventricular lead placement.

Figure 5:
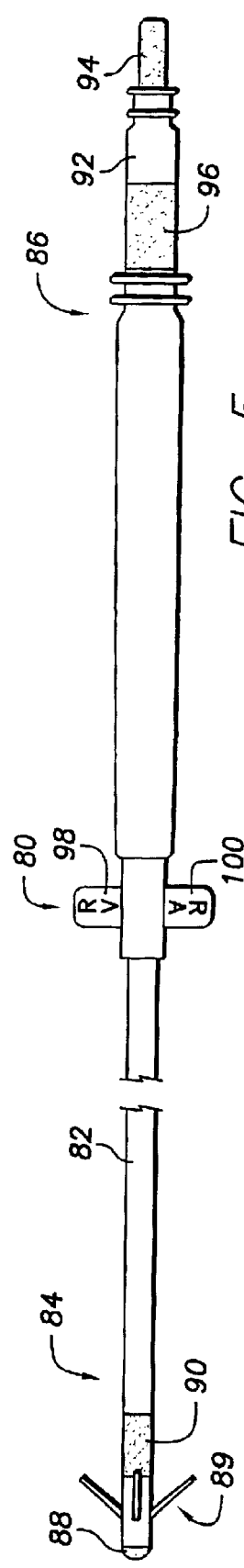
FIG. 5 is a side plan view of a further implantable cardiac lead embodying the present invention configured for placement in a right ventricle.
Figure 6:
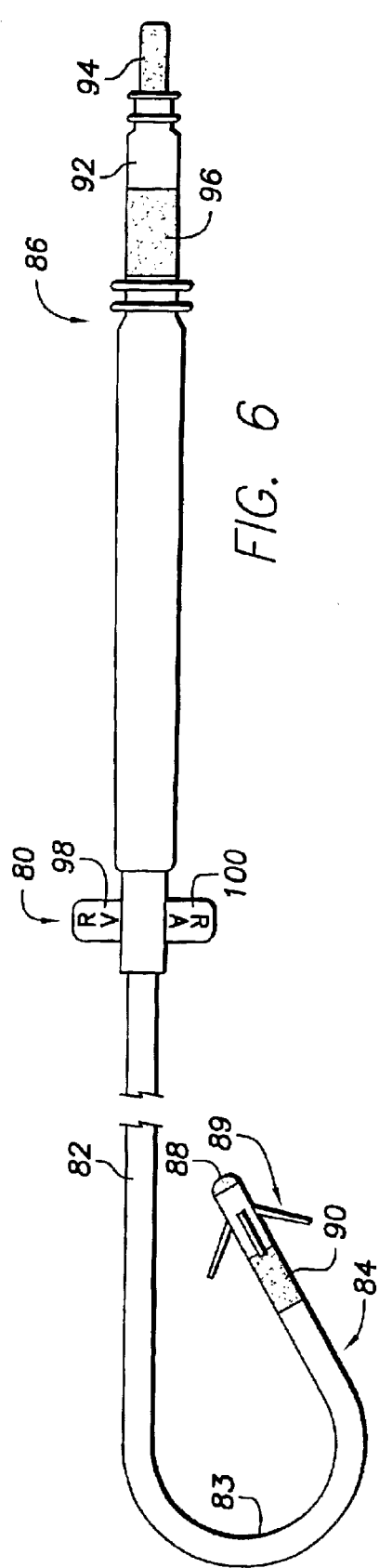
FIG. 6 is a side plan view of the lead of FIG. 5 configured for placement in the right atrium.

Other implantable cardiac leads 80 embodying the present invention are illustrated in FIGS. 5 and 6. In accordance with this embodiment, the lead 80, as illustrated in FIG. 5, is suitable for placement in the right ventricle of a heart while, as configured in FIG. 6, is suitable for placement in the right atrium of a heart. The lead 80 includes an elongated lead body 82 having a distal end 84 and a proximal end 86. As illustrated in FIG. 6, the lead 80 includes a "J"-shaped bend 83 at its proximal end 84 rendering the lead 80 suitable for placement in the right atrium as is known in the art, At the distal end 84, the lead body 82 has a pacing/sensing bipolar electrode pair including a tip electrode 88 and a ring electrode 90. Between the electrodes 88 and 90 is a tined anchoring mechanism 89 for anchoring the distal end 84 of the lead 80 in either the right ventricle or the right atrium. Such tined leads are well known in the art.

At the proximal end 86, the lead body 82 has a connector 92. The connector 92 includes a connection pin terminal 94 and a connection ring terminal 96. The connection pin 94 and ring 96 are coupled by lead conductors (not shown) to the tip electrode 88 and ring electrode 90, respectively, in a manner well known in the art. The connector 92 is configured to be received within a complimentarily shaped socket of an implantable cardiac stimulation device (not shown) in a known manner for coupling the tip electrode 88 and ring electrode 90 to internal sensing and pacing circuitry of the implantable device.

As in the previous embodiments, the proximal end 86 of the lead body 82 further includes a plurality of implant location indicators 98 and 100. Each of the implant location indicators includes a direct indication of a respective different one of the plurality of implant locations at which the electrodes 88 and 90, and hence the lead 80, may be implanted. For example, the indicator 98 includes a "RV" to provide a direct indication of the implant location within the right ventricle and the indicator 100 includes a "RA" to provide a direct indication of the implant location within the right atrium. Again, each of the implant location indicators is individually removable from the lead body 82. Hence, if the lead 80 is configured as illustrated in FIG. 5 for placement in the right ventricle, the indicator 100 may be removed to permit the indicator 98 to remain on the lead body for indicating that the lead 80 has been implanted in the right ventricle. If, however, the lead 80 is configured as illustrated in FIG. 6 for placement in the right atrium, the indicator 98 may be removed to permit the indicator 100 to provide an indication that the lead 80 has been implanted in the right atrium.

FIG. 7 shows the proximal end of an implantable cardiac lead 110 structured in accordance with another embodiment of the present invention. In accordance with this embodiment, the lead 110 is suitable for placement in either the right ventricle of the heart or the right atrium of the heart.

The lead 110 includes an elongated lead body 112 having a bipolar electrode pair (not shown) at a distal end (not shown). The bipolar electrode pair may be identical to any of the tip and ring electrodes of the bipolar electrode pairs previously described with respect to FIGS. 1 and 4–6. A connector 114 includes a connection pin terminal 116 coupled to the tip electrode and a connection ring terminal 118 coupled to the ring electrode.

The proximal end of the lead 110 further includes an implant location identifying member 120 which is fitted onto an extension 122 of the connector 114. As best seen in FIG. 8, the extension 122 has a generally square cross-section and the member 120 has an inner core 124 having a corresponding inner surface configuration to permit the member 120 to be fixedly retained on the connector extension 122.

The member 120 includes a plurality of implant location indicators which provide a direct indication of a respective different one of the plurality of implant locations. To that end, a face 126 of the member 120 has a "RV" thereon to provide a direct indication of the implant location within the right ventricle. An opposite face 128 may similarly have a "RA" thereon to provide a direct indication of the implant location within the right atrium.

The implant location indicators are individually selectable to provide a unique identification of the electrode or lead implant locations by a collar 130. The collar is slidable on the lead body 112 and includes a window 132. The collar has an inner surface complementary to the outer surface of the member 120 for being frictionally retained thereon. The window is located in the collar so as to be alignable with the implant location indicators on the member 120.

As may be best seen in FIG. 9, if the lead is implanted in the right ventricle, the collar is simply slid on the lead body 112 over the member 120 with the window 132 aligned with the face 126 of the member 120 having the "RV" implant location indicator thereon. This permits the right ventricular implant location indicator to be readily seen while the other implant location indicators are hidden by the collar 130. As a result, a direct and readily observable indication of the implant location of the lead 110 is provided for future reference.

FIG. 10 shows yet another lead 140 embodying the present invention. This lead 140 is suitable for providing both sensing/pacing and tachyarrhythmia termination stimulation delivery in a plurality of different locations of the heart such as the right ventricle or right atrium. The lead 140 has a distal end 144 and a proximal end 146. The lead 140 further includes an elongated lead body 142. At the distal end 144 of the lead body 142, the lead 140 includes a bipolar electrode pair including a tip electrode 148 having a fixation helix 150, and a ring electrode 152. The electrodes 148 and 152 provide bipolar sensing of electrical activity of the heart and pacing pulse delivery to the heart. Also at the distal end 144 of the lead 140, the lead body 142 carries an elongated shock coil 154 for delivering tachyarrhythmia termination stimulation pulses to the heart.

At the proximal end 146 of the lead 140, the lead 140 includes a first connector 156 and a second connector 158. The first connector 156 includes a connection pin terminal 160 and a connection ring terminal 162. The second connector 158 includes a connection pin terminal 164.

FIG. 11 shows a sectional view of the lead body 142. The lead body 142 is formed on a biocompatible insulation 166 having formed therein a central channel 168 and a plurality of lumens 170, 172, and 174. The central channel 168 accommodates a stylet coil 176 formed of electrically conductive material which both accommodates a stylet during implant of the lead 140 in a manner well known in the art and couples the tip electrode 148 to the connection pin 160. Lumen 170 accommodates a conductor 178 which couples the ring electrode 152 to the ring electrode 162. Lastly, lumens 172 and 174 accommodate conductors 180 and 182 which together couple the elongated shock coil 154 to the connection pin 164.

As in the embodiment of FIGS. 7–9, the lead 140 includes a lead implant location identifier 184 which includes an implant location identification member 186 and a collar 188 having a window 190 for selecting one of the lead implant location indicators carried by the lead implant location identification member 186. The member 186 and the collar 188 operate together in the same manner as the member 126 and collar 130 illustrated in FIGS. 7–9 to provide a direct indication of the implant location of the lead 140 for future reference.

FIG. 12 shows a lead 200 similar to lead 20 of FIG. 1 whose distal tip is suitable for placement in a plurality of different implant locations of a heart including an implant location in veins overlying the left ventricle of a heart within a distal coronary vein or an implant location adjacent the left atrium of the heart within the coronary sinus vein. Like lead 20, the lead 200 includes an elongated lead body 202 having a distal end 204 and a proximal end 206. At the distal end 204, the lead body 202 has a pacing/sensing bipolar electrode pair including a tip electrode 208 and a ring electrode 210. At the proximal end 206, the lead body 202 has a connector 212. The connector 212 includes a connection pin terminal 214 and a connection ring terminal 216. The connection pin 214 and connection ring 216 are coupled to the tip electrode 208 and ring electrode 212, respectively, by conductors (not shown) in a manner well known in the art.

In accordance with further aspects of the present invention, the lead 200 includes an implant location identifier 222 which is individually secured to the lead body 202 by a suture 234. The lead implant location identifier 222 is one of a plurality of lead implant location Identifiers which may be provided as an implant location identifying system along with the lead 200. Such a system 220 is illustrated in FIG. 13.

As may be seen in FIG. 13, the system 220 includes a plurality of implant location indicators including the indicator 222 and indicators 224 and 226. Each of the implant location indicators provides a direct indication of a respective different one of the plurality of implant locations in which the lead 200 may be implanted. For example, the indicator 222 carries a "LV" for indicating the lead implant location in the vein overlying the left ventricle within a distal coronary vein and indicator 224 carries a "LA" indicating the lead implant location adjacent the left atrium in the coronary sinus vein. The additional lead implant location indicator 226 may include an indication of a still further different lead implant location.

Each of the lead implant location indicators 222, 224, and 226 are generally cylindrical in configuration for individual retainment on the lead body 202 of the lead 200. To that end, each of the indicators 222, 224, and 226 includes a co-extensive slit 223, 225, and 227, respectively, and is formed of a biocompatible flexible material such as silicone. This permits the indicators to be spread apart for being fitted over the lead body 202 of the lead 20. Additionally, each of the lead implant location indicators 222, 224, and 226 includes a circumferential slot 229, 231, and 233 for receiving a suture for retaining an indicator to the lead body 202 of the lead 200.

Hence, in accordance with this further embodiment of the present invention, an implant location identifying system is provided for use with an implantable cardiac lead suitable for placement in any one of a plurality of different implant locations of a heart. Each of the plurality of implant location indicators provides a direct indication of a respective different one of the plurality of implant locations and is configured for retainment on the lead to provide a direct and readily observable indication of the implant location of the lead on which the lead implant location indicator is retained for future reference.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practice otherwise than as specifically described herein.

What is claimed is:

1. A method of implanting a cardiac lead, the method comprising:

advancing the lead to a site; and after advancing the lead, manipulating an identifier on the lead in a manner based on the site;

wherein manipulating comprises removing a first identifier from the lead so that a second identifier remains on the lead.

2. The method of claim 1, wherein the first identifier refers to at least one of a right atrium, right ventricle, left atrium, and left ventricle, and wherein the second identifier refers to at least one of a right atrium, right ventricle, left atrium, and left ventricle second.

3. A method of implanting a cardiac lead, the method comprising:

manipulating an identifier on the lead in a manner based on an intended site; and after manipulating the identifier, advancing the lead to the intended site;

wherein manipulating comprises removing a first identifier from the lead so that a second identifier remains on the lead.

4. The method of claim 3, wherein the intended site is at least one of a right atrium, right ventricle, left atrium, and left ventricle.

5. A method of implanting a cardiac lead, the method comprising:

providing a cardiac lead with at least one identifier that comprises location-related indicia;

advancing the lead to a site; and manipulating at least one of the at least one identifiers based on the site and the location-related indica;

wherein manipulating comprises removing a first identifier from the lead so that a second identifier remains on the lead.

6. The method of claim 5, wherein the location-related indica refers to at least one of a right atrium, right ventricle, left atrium, and left ventricle.

* * * * *